United States Patent [19]

Whitaker

[11] Patent Number: 5,324,264

[45] Date of Patent: Jun. 28, 1994

[54] SELF-CAPPING SYRINGE

[76] Inventor: Joseph Whitaker, P.O. Box 90340, Honolulu, Hi. 96835-0340

[21] Appl. No.: 79,924

[22] Filed: Jun. 23, 1993

[51] Int. Cl.$^5$ .................................................. A61M 5/00
[52] U.S. Cl. ...................................... 604/110; 604/111; 604/198
[58] Field of Search ............... 604/110, 111, 187, 192, 604/198, 263

[56] References Cited

U.S. PATENT DOCUMENTS

| | | | |
|---|---|---|---|
| 3,973,554 | 8/1976 | Tipton | 604/111 |
| 4,666,435 | 5/1987 | Braginetz | 604/198 |
| 4,743,233 | 5/1988 | Schneider | 604/192 |
| 4,943,282 | 7/1990 | Page et al. | 604/198 |
| 5,106,380 | 4/1992 | Lobello | 604/263 X |

*Primary Examiner*—John D. Yasko
*Attorney, Agent, or Firm*—Michael I. Kroll

[57] ABSTRACT

A self-capping syringe is provided, which consists of a barrel having a first end and a second end. A finger flange is on the first end and a needle hub is on the second end of the barrel. A plunger slides within the barrel and extends from the finger flange, while a thumb rest is on an outer end of the plunger. A needle extends axially outward from the needle hub on the second end of the barrel. A protective cap is also provided. A mechanism is for allowing the protective cap to twist upon the barrel from a retracted position that exposes the needle to an extended position which covers the needle. A structure is for locking the protective cap in the extended position after use, so as to prevent an accidental needle stick before disposal.

5 Claims, 2 Drawing Sheets

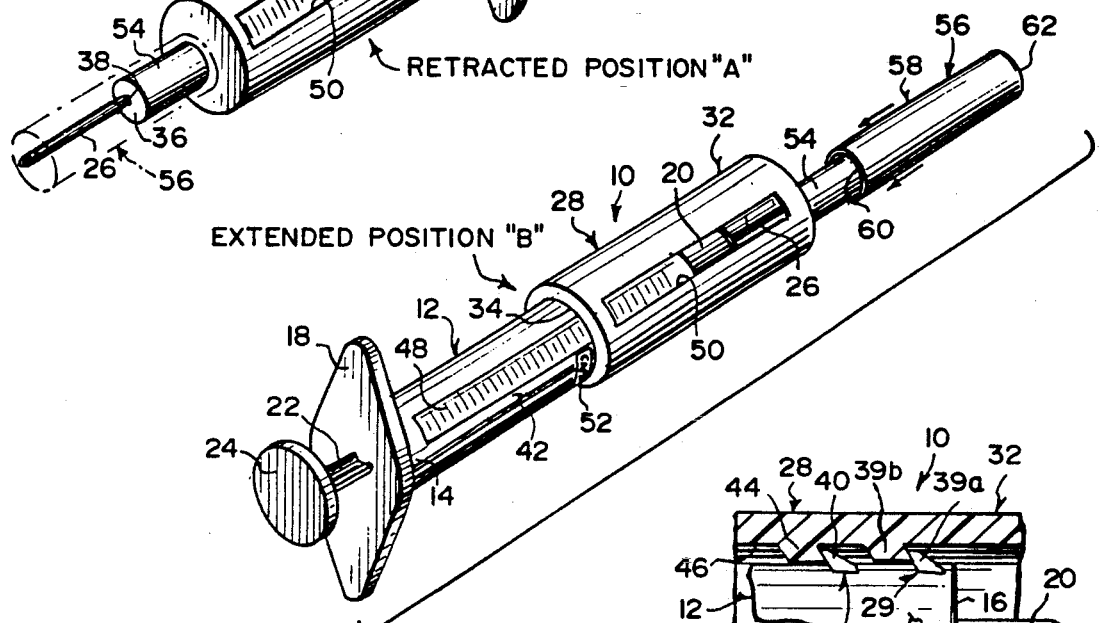

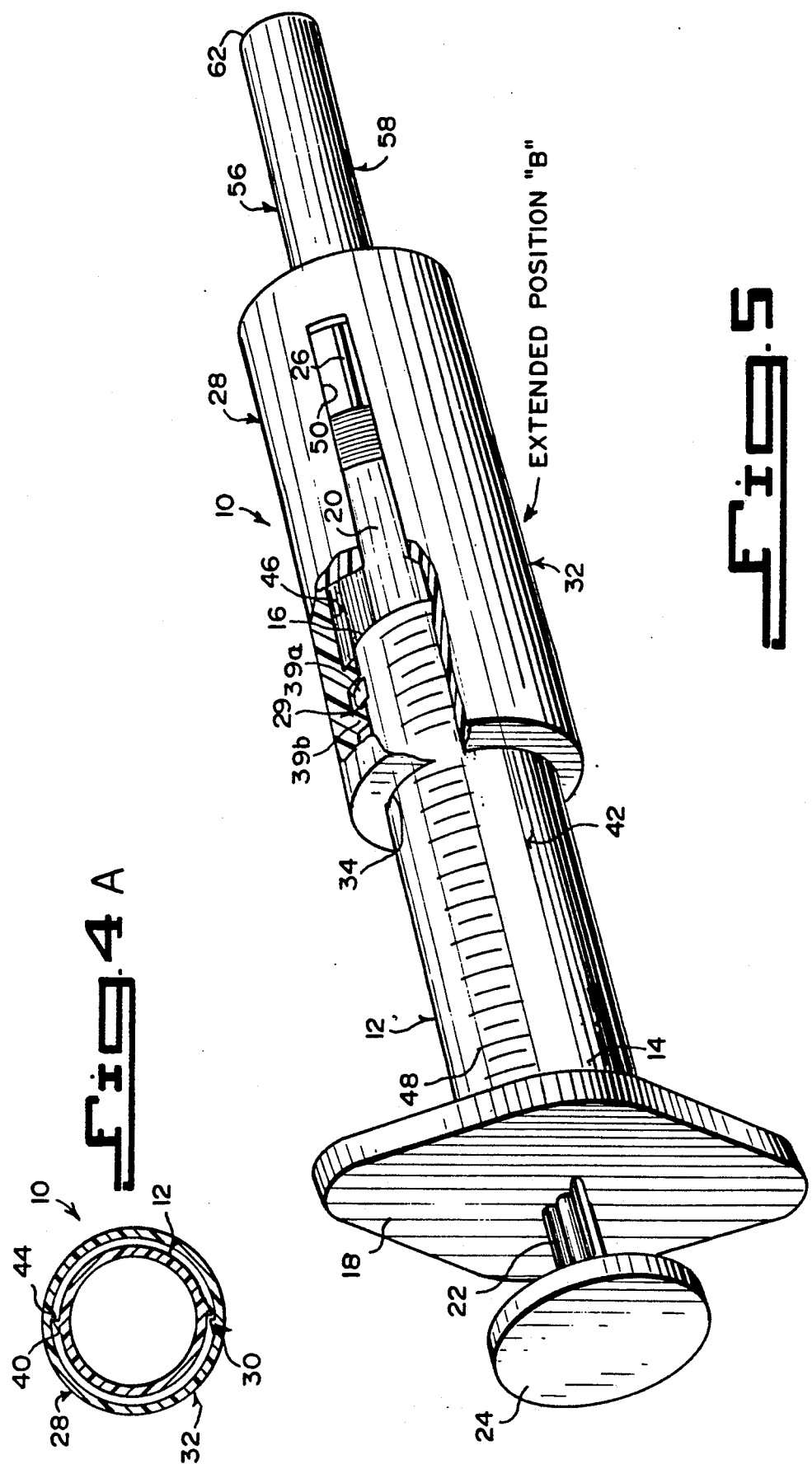

SELF-CAPPING SYRINGE

BACKGROUND OF THE INVENTION

1. Field of the Invention

The instant invention relates generally to hypodermic syringes and more specifically it relates to a self-capping syringe.

2. Description of the Prior Art

Numerous hypodermic syringes have been provided in prior art that are adapted to include safety covers for the needles, so that the hypodermic syringes can be safely disposed of. While these units may be suitable for the particular purpose to which they address, they would not be as suitable for the purposes of the present invention as heretofore described.

SUMMARY OF THE INVENTION

A primary object of the present invention is to provide a self-capping syringe that will overcome the shortcomings of the prior art devices.

Another object is to provide a self-capping syringe which contains a protective cap having a sleeve that is threaded upon a barrel of the syringe, so that after use the sleeve can be manually twisted into a locked position, to extend over the needle preventing an accidental needle stick.

An additional object is to provide a self-capping syringe in which a sheath can be utilized to fit over a reduced portion of the sleeve of the protective cap when in the extended position, for additional safety before disposal, while the sheath can also be placed on the reduced portion of the sleeve when in the retracted position when the needle is exposed for safety prior to use.

A further object is to provide a self-capping syringe that is simple and easy to use.

A still further object is to provide a self-capping syringe that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

FIG. 1 is a front perspective view of the instant invention showing the protective cap in a retracted position, whereby a sheath shown in phantom, may be installed on a reduced portion to prevent injuries prior to use.

FIG. 2 is a rear perspective view of the instant invention showing the protective cap in an extended locked position and a sheath being inserted onto a reduce portion thereof.

FIG. 3 is a side view of the instant invention with parts broken away, showing the protective cap in the locked extended position and the sheath ready to be inserted onto the reduce portion.

FIG. 4 is an enlarged view as indicated by arrow 4 in FIG. 3, showing the engaging locking tabs and threads in greater detail.

FIG. 4A is a cross sectional view taken along line 4A—4A in FIG. 3 with parts removed and left out for clarity, showing the engaging locking tabs between the sleeve of the protective cap and the barrel of the syringe.

FIG. 5 is an enlarged rear perspective view of the instant invention with parts broken away, showing the protective cap in the locked extended position and the sheath inserted onto the reduced portion.

DETAILED DESCRIPTION OF THE PREFERRED EMBODIMENTS

Turning now descriptively to the drawings, in which similar reference characters denote similar elements throughout the several views, FIGS. 1 through 5 illustrate a self-capping syringe 10, which consists of a barrel 12 having a first end 14 and a second end 16. A finger flange 18 is on the first end 14 of the barrel 12 and a needle hub 20 is on the second end 16 of the barrel 12. A plunger 22 slides within the barrel 12 and extends from the finger flange 18 on the first end 14 of the barrel 12, while a thumb rest 24 is on an outer end of the plunger 22. A needle 26 extends axially outward from the needle hub 20 on the second end 16 of the barrel 12. A protective cap 28 is also provided. A mechanism 29 is for allowing the protective cap 28 to twist upon the barrel 12 from a retracted position "A", that exposes the needle as shown in FIG. 1 to an extended position "B" which covers the needle 26 as shown in FIGS. 2, 3 and 5. A structure 30 is for locking the protective cap 28 in the extended position "B" after use, so as to prevent an accidental needle stick before disposal.

The protective cap 28 is a sleeve 32 having a first opened end 34 to receive the barrel 12 therein and a second closed end 36 with a small hole 38 therethrough, to allow the needle 26 to extend through the small hole 38 in the second closed end 36, when the protective cap 28 is in the retracted position "A".

The twist allowing mechanism 29 includes a first set of threads 39a on an outer surface 42 of the barrel 12. A second set of threads 39b are on an inner surface 46 of the sleeve 32 which engage with the first set of threads 39a.

The locking structure 30 includes a first set of locking tabs 40 on the outer surface 42 of the barrel 12 adjacent the second end 16 of the barrel 12. A second set of locking tabs 44 are on the inner surface 46 of the sleeve 32 adjacent the first opened end 34 of the sleeve 32. When the protective cap 28 is in the extended position "B", the first set of locking tabs 40 will engage with the second set of locking tabs 44, to retain the protective cap 28 in the extended position "B" and prevent accidental separation of the protective cap 28 from the barrel 12.

The barrel 12 has scale markings 48 thereon, while the sleeve 32 has a longitudinal window slot 50 therethrough. The scale markings 48 are visible through the longitudinal window slot 50, when the protective cap 28 is in the retracted position "A", as shown in FIG. 1.

The barrel 12 has an indicator 52 thereon located somewhat between the first end 14 and the second end 16. When the protective cap 28 is in the retracted position "A", the indicator 52 will not be visible. When the protective cap 28 is in the extended position "B", the indicator 52 will be visible to show that the protective cap 28 is completely in the extended position "B". The indicator 52 is a sign that contains the word "CAPPED" thereon.

The protective cap 28 further includes the sleeve 32 having a reduced portion 54 of a smaller diameter at the second closed end to encircle the needle 26, when the protective cap 28 is in the extended position "B". A sheath 56 can fit over the reduced portion 54 of the sleeve 32, when the protective cap 28 is in the extended position "B" for additional safety before disposal. The sheath 56 may also be used to cover the exposed needle 26, when the protective cap 28 is in the retracted position "A" prior to use. The sheath 56 is a hollow tube 58, having a first opened end 60 to receive the reduced portion 54 of the sleeve 32 therein and a second closed end 62, so as to cover over the small hole 38 in the second closed end 36 of the sleeve 32. The length of the hollow tube 58 will also allow coverage of the needle 26, when placed upon the reduced portion 54 in the retracted position "A" for prevention of injuries prior to use.

As best shown in FIGS. 4 and 4A, the first set of locking tabs 40 are tapered and face inwardly. The second set of locking tabs 44 are tapered in an opposite direction than the first set of locking tabs 40 and face outwardly. Once the first set of locking tabs 40 mate with the second set of locking tabs 44, the protective cap 28 will be permanently retained in the extended position "B".

OPERATION OF THE INVENTION

The self-capping syringe 10 will come with the protective cap 28 in the retracted position "A" as indicated in FIG. 1. The self-capping syringe 10 can be used as a person uses a standard hypodermic syringe. The protective cap 28 is then manually twisted down into the extended position "B" as indicated in FIGS. 2, 3 and 5. The reduced portion 54 of the sleeve 32 will now cover the needle 26, to prevent an accidental needle stick before disposal. As an additional safety before disposal the sheath 56 can now be inserted onto the reduced portion 54, to cover over the small hole 38.

LIST OF REFERENCE NUMBERS

10—self-capping syringe
12—barrel
14—first end of 12
16—second end of 12
18—finger flange on 14
20—needle hub on 16
22—plunger in 12
24—thumb rest on 22
26—needle on 20
28—protective cap on 12
29—twist allowing mechanism
30—locking structure
32—sleeve
34—first opened end of 32
36—second closed end of 32
38—small hole in 36
39a—threads on 42
39b—threads on 46
40—locking tab on 42
42—outer surface of 12
44—locking tab on 46
46—inner surface of 32
48—scale markings on 12
50—longitudinal window slot in 32
52—indicator
54—reduced portion of 32
56—sheath
58—hollow tube of 56
60—first opened end of 58
62—second closed end of 58
"A"—retracted position
"B"—extended position It will be understood that each of the elements described above, or two or more together may also find a useful application in other types of methods differing from the type described above.

While certain novel features of this invention have been shown and described and are pointed out in the annexed claims, it is not intended to be limited to the details above, since it will be understood that various omissions, modifications, substitutions and changes in the forms and details of the device illustrated and in its operation can be made by those skilled in the art without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed is new and desired to be protected by Letters Patent is set forth in the appended claims:

1. A self-capping syringe which comprises:
   a) a barrel having a first end and a second end;
   b) a finger flange on said first end of said barrel;
   c) a needle hub on said second end of said barrel;
   d) a plunger which slides within said barrel and extends from said finger flange on said first end of said barrel;
   e) a thumb rest on an outer end of said plunger;
   f) a needle extending axially outward from said needle hub on said second end of said barrel;
   g) a protective cap, said protective cap is a sleeve having a first opened end to receive said barrel therein and a second closed end with a small hole therethrough to allow said needle to extend through said small hole in said second closed end, when said protective cap is in said retracted position, said twist allowing means includes a first set of threads on an outer surface of said barrel, and a second set of threads on an inner surface of said sleeve which engage with said first set of threads;
   h) means for allowing said protective cap to twist upon said barrel from a retracted position that exposes said needle to an extended position which covers said needle;
   i) means for locking said protective cap in said extended position after use, so as to prevent an accidental needle stick before disposal, said locking means includes a first set of locking tabs on said outer surface of said barrel adjacent said second end of said barrel, and a second set of locking tabs on said inner surface of said sleeve adjacent said first opened end of said sleeve, so that when said protective cap is in said extended position said first set of locking tabs will engage with said second set of locking tabs, to retain said protective cap in said extended position and prevent accidental separation of said protective cap from said barrel;
   j) further including said barrel having scale markings thereon, and said sleeve having a longitudinal window slot therethrough, so that said scale markings are visible through said longitudinal window slot, when said protective cap is in said retracted position; and k) further including said barrel having an indicator thereon located somewhat between said first end and said second end, so that when said protective cap is in said retracted position said indicator will not be visible and when said protective cap is in said extended position said indicator will be visible to show that said protective cap is completely in said extended position, said indicator is a sign that contains the word "CAPPED" thereon.

2. A self-capping syringe as recited in claim 1, wherein said protective cap further includes said sleeve having a reduced portion of a smaller diameter at said second closed end to encircle said needle, when said protective cap is in said extended position.

3. A self-capping syringe as recited in claim 2, further including a sheath to fit over said reduced portion of said sleeve, when said protective cap is in said extended position for additional safety before disposal, whereby said sheath may also be used to cover said exposed needle when said protective cap is in said retracted position prior to use.

4. A self-capping syringe as recited in claim 3, wherein said sheath is a hollow tube having a first opened end to receive said reduced portion of said sleeve therein and a second closed end, so as to cover over said small hole in said second closed end of said sleeve, whereby the length of said hollow tube will also allow coverage of said needle when placed upon said reduced portion in said retracted position for prevention of injuries prior to use.

5. A self-capping syringe as recited in claim 4, further including:
   a) said first set of locking tabs are tapered and face inwardly; and
   b) said second set of locking tabs are tapered in an opposite direction than said first set of locking tabs and face outwardly, so that once said first set of locking tabs mate with said second set of locking tabs, said protective cap will be permanently retained in said extended position.

* * * * *